United States Patent
Andersen et al.

(10) Patent No.: US 9,681,985 B2
(45) Date of Patent: Jun. 20, 2017

(54) SYSTEM AND METHOD FOR MINIMALLY TRAUMATIC OPHTHALMIC PHOTOMEDICINE

(75) Inventors: Dan E. Andersen, Menlo Park, CA (US); David H. Mordaunt, Los Gatos, CA (US)

(73) Assignee: TOPCON MEDICAL LASER SYSTEMS, INC., Santa Clara, CA (US)

(*) Notice: Subject to any disclaimer, the term of this patent is extended or adjusted under 35 U.S.C. 154(b) by 2243 days.

(21) Appl. No.: 11/606,451

(22) Filed: Nov. 29, 2006

(65) Prior Publication Data

US 2007/0129709 A1     Jun. 7, 2007

Related U.S. Application Data

(60) Provisional application No. 60/742,024, filed on Dec. 1, 2005.

(51) Int. Cl.
*A61F 9/008* (2006.01)
*A61F 9/007* (2006.01)

(52) U.S. Cl.
CPC .......... *A61F 9/008* (2013.01); *A61F 9/00821* (2013.01); *A61F 9/00781* (2013.01); *A61F 2009/00863* (2013.01); *A61F 2009/00868* (2013.01); *A61F 2009/00872* (2013.01); *A61F 2009/00897* (2013.01)

(58) Field of Classification Search
USPC ......................................... 606/4, 5; 128/898
See application file for complete search history.

(56) References Cited

U.S. PATENT DOCUMENTS

| | | |
|---|---|---|
| 3,703,176 A | 11/1972 | Vassiliadis et al. |
| 3,883,235 A | 5/1975 | Lynn et al. |
| 4,391,275 A | 7/1983 | Fankhauser et al. |
| 4,536,065 A | 8/1985 | Sheingorn |
| 4,685,784 A | 8/1987 | Kirchhuebel |
| 4,884,884 A | 12/1989 | Reis |
| 4,901,718 A | 2/1990 | Bille et al. |
| 4,907,586 A | 3/1990 | Bille et al. |

(Continued)

FOREIGN PATENT DOCUMENTS

| | | |
|---|---|---|
| EP | WO 95/27453 | 10/1995 |
| EP | WO 00/21475 | 4/2000 |

(Continued)

OTHER PUBLICATIONS

U.S. Appl. No. 12/045,635, filed Mar. 2008, Palankar.

(Continued)

*Primary Examiner* — William Thomson
*Assistant Examiner* — Qingjun Kong
(74) *Attorney, Agent, or Firm* — Morrison and Foerster, LLP

(57) ABSTRACT

A system and method for treating ophthalmic target tissue in which a light source generates a beam of light, a scanner unit deflects the beam of light into a pattern, a beam delivery unit for delivering the pattern to ophthalmic target tissue. The light is either pulsed or moved across the target tissue such that the light pulses having a duration of, or the light dwells on any given point of target tissue for, between 30 μs and 10 ms.

12 Claims, 4 Drawing Sheets

(56) References Cited

U.S. PATENT DOCUMENTS

| | | | |
|---|---|---|---|
| 4,917,486 A | | 4/1990 | Raven et al. |
| 5,144,630 A | * | 9/1992 | Lin ................................. 372/22 |
| 5,293,532 A | | 3/1994 | Marshall |
| 5,302,259 A | | 4/1994 | Birngruber |
| 5,336,216 A | | 8/1994 | Dewey |
| 5,347,326 A | * | 9/1994 | Volk ......................... 351/160 R |
| 5,391,165 A | | 2/1995 | Fountain et al. |
| 5,425,729 A | | 6/1995 | Ishida et al. |
| 5,480,396 A | | 1/1996 | Simon et al. |
| 5,514,127 A | | 5/1996 | Shanks |
| 5,543,866 A | | 8/1996 | Van De Velde |
| 5,549,596 A | * | 8/1996 | Latina ............................... 606/4 |
| 5,568,208 A | | 10/1996 | Van De Velde |
| 5,618,285 A | | 4/1997 | Zair |
| 5,688,264 A | | 11/1997 | Ren et al. |
| 5,743,902 A | | 4/1998 | Trost |
| 5,748,352 A | | 5/1998 | Hattori |
| 5,886,768 A | | 3/1999 | Knopp et al. |
| 5,892,569 A | | 4/1999 | Van De Velde |
| 5,921,981 A | | 7/1999 | Baymanyar et al. |
| 5,943,117 A | | 8/1999 | Van De Velde |
| 5,957,915 A | | 9/1999 | Trost |
| 5,971,978 A | | 10/1999 | Mukai |
| 5,980,513 A | | 11/1999 | Frey et al. |
| 6,011,563 A | | 1/2000 | Fournier |
| 6,059,772 A | * | 5/2000 | Hsia et al. ......................... 606/4 |
| 6,066,128 A | | 5/2000 | Bahmanyar et al. |
| 6,096,028 A | | 8/2000 | Bahmanyar et al. |
| 6,099,522 A | | 8/2000 | Knopp et al. |
| 6,149,644 A | | 11/2000 | Xie |
| 6,186,628 B1 | | 2/2001 | Van De Velde |
| 6,267,756 B1 | | 7/2001 | Feuerstein et al. |
| 6,328,733 B1 | | 12/2001 | Trost |
| RE37,504 E | * | 1/2002 | Lin ................................. 606/5 |
| 6,347,244 B1 | | 2/2002 | Dubnack |
| 6,494,878 B1 | | 12/2002 | Pawlowski et al. |
| 6,514,241 B1 | | 2/2003 | Hsia |
| 6,607,527 B1 | | 8/2003 | Ruiz et al. |
| 6,620,154 B1 | | 9/2003 | Amirkhanian et al. |
| 6,682,523 B2 | | 1/2004 | Shadduck |
| 6,698,886 B2 | | 3/2004 | Pollack et al. |
| 6,705,726 B2 | | 3/2004 | Tanassi et al. |
| 6,726,679 B1 | | 4/2004 | Dick et al. |
| 6,733,490 B1 | | 5/2004 | Falsini et al. |
| 6,789,900 B2 | | 9/2004 | Van De Velde |
| 6,942,343 B2 | | 9/2005 | Farberov |
| 7,115,120 B2 | | 10/2006 | Lin |
| 7,125,119 B2 | | 10/2006 | Farberov |
| 7,146,983 B1 | | 12/2006 | Hohla et al. |
| 2003/0009155 A1 | | 1/2003 | Pawlowski et al. |
| 2003/0109907 A1 | | 6/2003 | Shadduck |
| 2003/0179344 A1 | * | 9/2003 | Van de Velde ................ 351/200 |
| 2004/0215175 A1 | | 10/2004 | Feklistov et al. |
| 2005/0096639 A1 | * | 5/2005 | Slatkine et al. ................... 606/5 |
| 2005/0143716 A1 | | 6/2005 | Vinciguerra et al. |
| 2005/0159662 A1 | * | 7/2005 | Imanishi et al. ............. 600/473 |
| 2005/0288745 A1 | | 12/2005 | Andersen et al. |
| 2006/0050229 A1 | * | 3/2006 | Farberov ....................... 351/161 |
| 2006/0100677 A1 | | 5/2006 | Blumenkranz et al. |

FOREIGN PATENT DOCUMENTS

| | | |
|---|---|---|
| EP | WO 03/003955 | 5/2003 |
| EP | 1354573 A1 | 10/2003 |
| JP | 2003532483 | 11/2003 |
| JP | 2004-121814 A | 4/2004 |
| WO | WO 0185044 A1 | 11/2001 |

OTHER PUBLICATIONS

Carlslaw, H.S., Jaeger, J.C., "Conduction of Heat in Solids", 2nd ed., Oxford University Press, 1959, pp. 92-132.

Naess et al., "Computer-Assisted Laser Photocoagulation of the Retina—a Hybrid Tracking Approach", *Journal of Biomedical Optics*, Apr. 2002, vol. 7, No. 2, pp. 179-189.

Markow, M.S. et al., "An Automated Laser System for Eye Surgery", *IEEE Engineering in Medicine & Biology Magazine*, vol. 8, Dec. 1989, pp. 24-29.

Wright, Cameron et al., "Hybrid Approach to Retinal Tracking and Laser Aiming for Photocoagulation", *Journal of Biomedical Optics* 2(2), Apr. 1997, pp. 195-203.

Barrett, Steven et al., "Computer-Aided Retinal Photocoagulation System", *Journal of Biomedical Optics* 1(1), Jan. 1996, pp. 83-91.

Van de Velde, "Role of the Scanning Laser Ophthalmoscope in Photodynamic Therapy of Macular Disease", *Ophthalmic Technologies X, Proceedings of SPIE*, vol. 3908 (2000), pp. 190-201.

Barrett, Steven F. et al., "Digital Imaging-Based Retinal Photocoagulation System", *SPIE*, vol. 2971, pp. 118-128.

Wright, Cameron et al., "Initial In Vivo Results of a Hybrid Retinal Photocoagulation System", *Journal of Biomedical Optics*, vol. 5, No. 1, Jan. 2000, pp. 56-61.

Schuele, George, et al., "RPE Damage Thresholds and Mechanisms for Laser Exposure in the Microsecond-To-Millisecond Time Regimen", *Investigative Ophthalmology & Visual Science*, Feb. 2005, vol. 46, No. 2.

Abstract of WO 0185044 A1, publication date Nov. 15, 2001, downloaded from espacenet.com database on Feb. 9, 2010.

International Preliminary Report on Patentability received for PCT Patent Appltcation No. PCT/US2005/023696, issued on Feb. 17, 2009, 4 pages.

International Search Report and Written Opinion received for PCT Patent Application No. PCT/US2005/023696, mailed on Jun. 13, 2008, 4 pages.

Supplementary European Search Report received for European Patent Application No. 05769199.0, mailed on Aug. 19, 2009, 3 pages.

International Search Report and Written Opinion received for PCT Patent Application No. PCT/US2006/45957, mailed on Jul. 27, 2007, 5 pages.

International Preliminary Report on Patentability received for PCT Patent Application No. PCT/US2006/45957, issued on Jun. 3, 2008, 5 pages.

International Search Report and Written Opinion received for PCT Patent Application No. PCT/US2008/03243, mailed on Jul. 14, 2008, 6 pages.

International Preliminary Report on Patentability received for PCT Patent Application No. PCT/US2008/003243, issued on Sep. 15, 2009, 6 pages.

Extended European Search Report received for European Patent Application No. 08726727.4, mailed on Mar. 5, 2011, 6 pages.

* cited by examiner

SYSTEM AND METHOD FOR MINIMALLY TRAUMATIC OPHTHALMIC PHOTOMEDICINE

This application claims the benefit of U.S. Provisional Application No. 60/742,024, filed Dec. 1, 2005, which is incorporated herein by reference.

FIELD OF THE INVENTION

The present invention provides apparatus, methods and systems of their use for the targeted photothermal treatment of ocular structures, for example, the layers adjacent to the retinal pigmented epithelium and those of the trabecular meshwork. It is particularly useful in the treatment of a variety of retinal disorders, as well as ocular hypertension.

BACKGROUND OF THE INVENTION

Laser photomedicine is a well-established therapeutic modality for a wide variety of conditions. To date, the use of ophthalmic lasers has been limited to either short (around one microsecond or shorter) pulse systems for sub-cellular targeting, or long (hundreds of microseconds and longer) pulse systems that indiscriminately denature relatively large volumes of tissue.

For example, present standard retinal photocoagulative treatment for conditions such as Diabetic Retinopathy, and Age-Related Macular Degeneration utilize visible laser light with exposure durations on the order of 100 ms. Generation of heat due to absorption of visible laser light occurs predominantly in the retinal pigmented epithelium (RPE) and pigmented choriocappilaris, the melanin containing layers directly beneath the photoreceptors of the sensory retina. FIG. 1 schematically illustrates the ocular structure around the melanin layer, which includes the RPE disposed between the sensory retina and the choroid. Due to heat diffusion during long exposures, this standard therapy also irreversibly damages the overlying sensory retina.

Although it does halt the progress of the underlying disease, such irreversible damage decreases the patient's vision by destroying not only the photoreceptors in the irradiated portion of the retina but also by creating permanent micro-scotomas, and possibly also damaging the retinal nerve fibers that traverse the targeted portion of the retina. Such nerve fiber damage eliminates the signals it would have carried from distal areas of the retina, thus unnecessarily further worsening the patient's vision.

The RPE may be thought of as a 10 µm thick monocellular structure containing a 4 µm thick layer of pigment. The characteristic thermal relaxation time ($\tau_r$) may be approximated by the relation:

$$\tau_r = d^2/4\alpha \qquad (1)$$

where d is the thickness of the layer and $\alpha$ is the tissue's thermal diffusivity (in this case that of water; 0.14 mm²s⁻¹), as discussed in H S Carlslaw, J C Jaeger, "Conduction of Heat in Solids" Second Edition, Oxford University Press, 1959. This shows that the entire RPE layer itself and the pigmented zone within it would have characteristic thermal relaxation times of approximately 180 µs and 30 µs, respectively. During a typical photocoagulative pulse of 100 ms, heat generated in the RPE and in pigmented choroid will diffuse to the distance of about 220 µm, thus leading to irreversible damage to the inner retina.

To ameliorate the abovementioned collateral damage unavoidably suffered by the use of "long" pulses, the use of a burst of microsecond or sub-microsecond pulses has been recently investigated. This approach yields purely photomechanical damage that can be confined to the pigmented organelles of the RPE (melanosomes). It is believed that such confined sub-cellular damage can instigate a wound healing response, which subsequently rebuilds the RPE without causing damage to the photoreceptors. Although it would be simpler to deliver such short pulses of sufficient energy to unequivocally damage the RPE cells themselves, rather than just the melanosomes, the energy required to do so at such short pulses very often ruptures Bruch's membrane, which is immediately behind the RPE. This ultimately worsens the condition. Such a technique has been described by Latina in U.S. Pat. No. 5,549,596, where the use of pulses that are of sufficiently short duration such that the heat produced by their absorption is confined to the absorbing (pigmented) cell alone is discussed. This approach is risky, however, as it endangers the integrity of the target and adjacent structures due to the photomechanical forces imparted. The relatively narrow therapeutic window in this approach, and lack of a visible endpoint of the treatment necessitate the use of specialized diagnostic devices to discern the appropriate retinal irradiance for each patient. Furthermore, difficulty in generating these short pulses, require relatively complicated, expensive, and delicate equipment, as compared to that of the systems for generating 100 ms pulse treatment.

The use of a pulse-train of near-infrared light from a semiconductor laser source has also been investigated in an attempt to limit the extent of photocoagulative damage to the outer retina. This approach makes use of the fact that biochemical damage is additive when created over time, and such time is relatively short when compared the body's response to that damage, such as is described in U.S. Pat. No. 5,302,259 by Birngruber. To date, the clinical results of such systems have been lackluster, even when used in conjunction with an exogenous dye to increase the absorption of the infrared light. Pulse trains of 810 nm light of a 200 ms overall duration and 10% duty cycle (typically 100 individual 200 µs pulses, uniformly spaced 1800 µs apart) have been used to damage the RPE. Due to heat accumulation during the train and non-specific absorption of the near infrared light, such treatment ultimately caused indiscriminate damage to large volumes of tissue because it simply acted as long pulse rather than an ensemble of "short" individual pulses.

Theoretical modeling by the inventors of the heating effects produced by 100, 500, and 1000 µs pulses directly in the RPE and tissue 5 µm away (the interface between the RPE and the outer sensory retina) is shown in FIG. 3. This type of thermal injury is well described by an Arrhenius molecular damage model. As is known in the art for such cases, the amount of molecular damage is only linearly dependent on the length of time a temperature is held, but exponentially dependent upon the ultimate temperature reached. With that in mind, one may consider that the differences in the peak temperatures achieved are an indicator of the spatial selectivity of these pulses.

Likewise, in photomedical treatments to alleviate the increased intraocular pressure associated with glaucoma either disproportionately long or short pulses are currently used. To date, similar to retinal treatments, the use of pulses on the order of 100 ms, 1 µs and 5 ns have been reported with varying degrees of overall clinical success. Here the target chromophore is pigment accumulated in the trabecular meshwork of the eye's anterior chamber, as shown schematically in FIG. 4. The sizes of the targeted structures in the trabecular meshwork are similar to those described above, thus the same pulse duration ranges are relevant there as well.

Accordingly, there is a need for a flexible, robust, cost-effective way to provide predictable and minimally traumatic ophthalmic photomedical treatment such as, but not limited to, the retina and trabecular meshwork that is not provided by known methods or devices.

SUMMARY OF THE INVENTION

The present invention solves the aforementioned problems by providing a system and method for treating ophthalmic target tissue using light having pulse durations or dwell times within a specific time period to provide superior treatment results.

A system for treating ophthalmic target tissue comprises a light source for generating a beam of light, a scanner unit for deflecting the beam of light into a pattern, wherein at least one of the light source and the scanner unit causing the beam of light to comprise a plurality of light pulses, and a beam delivery unit for delivering the plurality of light pulses to ophthalmic target tissue, wherein each of the plurality of light pulses having a duration between 30 μs and 10 ms.

In another aspect, a system for treating ophthalmic target tissue comprises a light source for generating a beam of light, a scanner unit for deflecting the beam of light into a pattern, and a beam delivery unit for delivering the deflected light beam to ophthalmic target tissue, wherein the scanner unit deflects the beam so that the beam dwells on any given point of the target tissue for between 30 μs and 10 ms.

A method of treating ophthalmic target tissue comprises generating a beam of light, deflecting the beam of light into a pattern, wherein at least one of the generating and the deflecting causing the beam of light to comprise a plurality of light pulses, and delivering the plurality of light pulses to ophthalmic target tissue, wherein each of the plurality of light pulses having a duration between 30 μs and 10 ms.

In another aspect, a method of treating ophthalmic target tissue comprises generating a beam of light, deflecting the beam of light into a pattern, and delivering the deflected light beam to ophthalmic target tissue, wherein the deflecting and the delivering are performed such that the beam dwells on any given point of the target tissue for between 30 μs and 10 ms.

Other objects and features of the present invention will become apparent by a review of the specification, claims and appended figures.

DETAILED DESCRIPTION OF THE PREFERRED EMBODIMENTS

Figure 1:
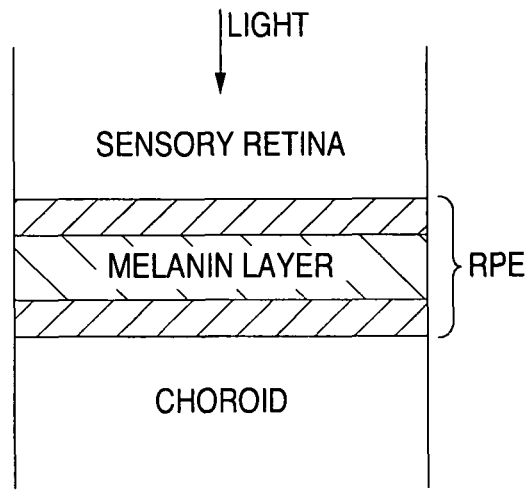
FIG. 1 is a schematic diagram illustrating the ocular structure around the melanin layer.
Figure 4:
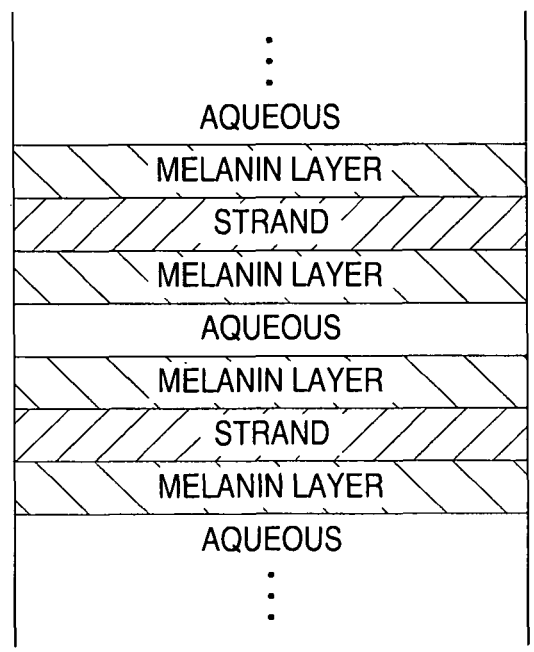
FIG. 4 is a schematic diagram illustrating the structure of the trabecular meshwork of the eye's anterior chamber.
Figure 2:
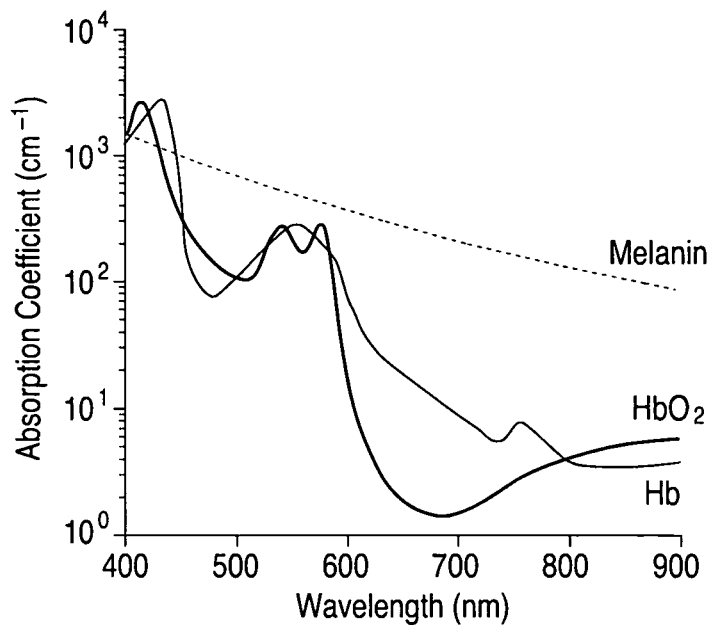
FIG. 2 is a graph illustrating the absorption spectra of predominant ocular chromophores, Melanin (RPE), and Hemoglobins (Choroid).
Figure 3:
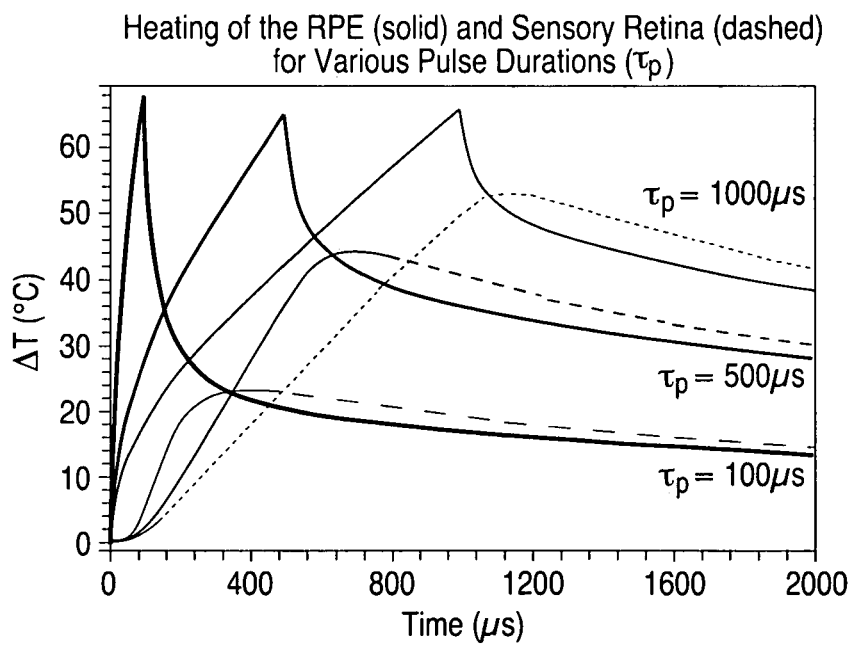
FIG. 3 is a graph with retinal heating theoretical curves showing the progressively increasing selectivity (thermal confinement) as the pulse duration decreases.
Figure 5:
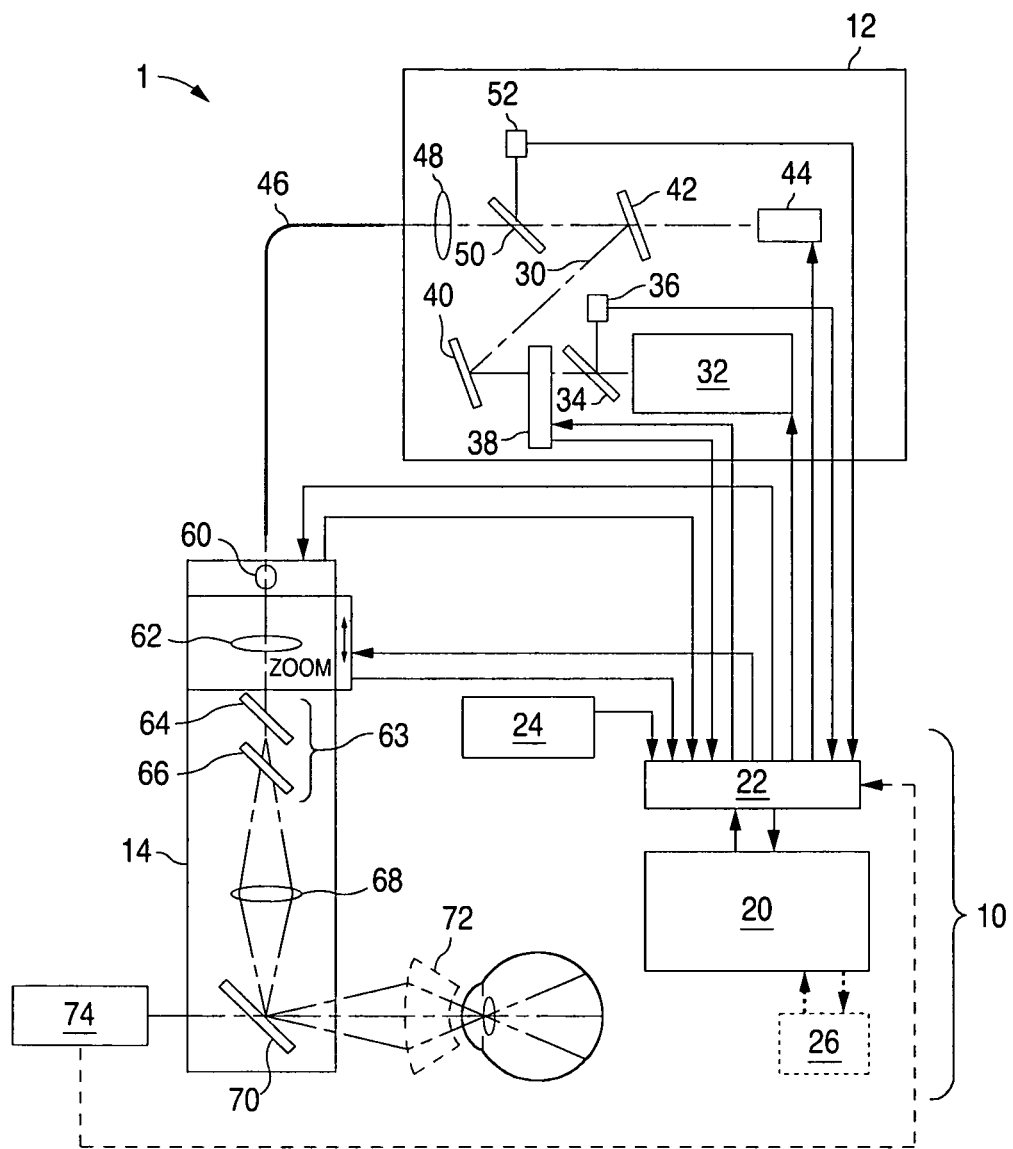
FIG. 5 is a diagram showing the elements of the light generating and scanning system for implementing the present invention.

The present invention is system and method to provide predictable and minimally traumatic ophthalmic photomedical treatment. FIG. 5 illustrates a system 1 for implementing the present invention, and includes a control unit 10, a light generation unit 12 and a light delivery unit 14. This system can provide either pulses of therapeutic light, or continuous scans of therapeutic light, to the eye of a patient.

The control unit 10 controls the disposition (generation and delivery) of the light, and includes control electronics 20 and resident a input and output 22, as shown. Likewise, input from an input device 24 (e.g. a joystick) and/or a graphic user interface 26, may be used by the control electronics 20 for controlling the light disposition.

In the light generation unit 12, a light beam 30 is generated by a light source 32, such as a 532 nm wavelength frequency-doubled, diode-pumped solid state laser. The beam 30 first encounters a mirror 34 which serves to sample the light for safety purposes, reflecting a fixed portion towards a photodiode 36 that measures its power. Following that, the light beam 30 encounters a shutter 38, mirror 40, and mirror 42. Shutter 38 fundamentally serves to control the delivery of the light beam 30. It may be used to gate the light, in addition to grossly blocking it. Mirror 40 is configured as a turning mirror as well as a combining mirror to combine aiming light from a second light source 44 with light beam 30. The aiming light is preferable coincident along the same path as the light beam 30 to provide a visual indication of where the treatment light from source 32 will be projected onto the target tissue. After mirror 42, the light beam 30 (now including any aiming light from source 44) is directed into an optical fiber 46 via a lens 48. An optional mirror 50 can be used to direct a portion of the light beam to a second photodiode 52, which serves purposes similar to those of mirror 34 and photodiode 36 as well as a redundant monitor of the state of shutter 38. Optical fiber 46 is a convenient way to deliver the light from the light generation unit 12 to the light delivery unit 14. However, free-space delivery of the light may be used instead, especially where the light generation and delivery units 12, 14 are integrally packaged together.

In the light delivery unit 14, lens 60 conditions the light exiting the optical fiber 46. Lens 60 may be a single lens, or a compound lens. If it is a compound lens, lens 60 may be made to be a zoom lens that adjusts the spot diameter of the beam. This is useful for easily adjusting the size of patterns and their elements on the target tissue as discussed further below. An additional lens 62 may be used to image the optical beam downstream, and possible act as the zoom lens as shown. The image point of lens 62 can be done to minimize the size of optical elements downstream. A scanner 63, preferably having a pair of scanning optics (i.e. movable mirrors, wedges, and/or lenses), is used to deflect the beam 30 to form a pattern P of spots or lines (straight or curved). Preferably, the scanning optics rotate or move in orthogonal X, Y directions such that any desired pattern P can be produced. A lens 68 focuses the beam onto a mirror 70 which redirects the beam through an ophthalmic lens 72 and onto the target tissue. Mirror 70 also provides for visualization of the target tissue therethrough, either directly by the physician or by a visualization device 74. More specifically, visualization may be accomplished by directly viewing the retina through mirror 70, or by creating a video image using a visualization device 74 (e.g. CCD camera) to be displayed either on a remote monitor, or, as indicated by the dashed line of FIG. 5, on the graphical user interface 26.

Ideally, the lens 62 images the beam to a midpoint between scanning optics 64, 66 and onto mirror 70. This may be done to minimize the size of the mirror 70 in an attempt to increase the overall solid angle subtended by the visualization device 74. When mirror 70 is small, it may be placed directly in the visualization path without much disturbance. It may also be placed in the center of a binocular imaging apparatus, such as a slit lamp biomicroscope, without disturbing the visualization. Lens 62 could also be placed one focal length away from the optical midpoint of the scanning optics 64, 66 to produce a telecentric scan. In this case, mirror 70 would need to be large enough to contain the entire scan, and could be made a high reflector spectrally matched to the output of light sources 32, 44, and visualization accomplished by looking through mirror 70. Of course, a further refinement would be to photopically balance the transmission of mirror 70 by using a more complicated optical coatings to make the colors appear more natural, rather than, say, pinkish, when using a green notch filter coating on mirror 70.

Ophthalmic lens 72 may be placed directly before the eye to aid in visualization, such as might be done with any ophthalmoscope, slitlamp biomicroscope, ftundus camera, scanning laser ophthalmoscope (SLO), or optical coherence tomography (OCT) system. Ophthalmic lens 72 may be a contact or non-contact lens, although a contact lens is preferred because it serves the additional purpose of dampening any of the patient's eye movement.

The pattern P of light formed by the scanning optics 64, 66 can be anything from a specifically located spot, an array of spots, or a continuous scan of lines or line segments. Light sources 32, 44 and/or shutter 38 may be gated on and off by commands from control electronics 20 via input and output 22 to produce discrete spots, or simply run cw to create continuous scans as a means to produce pattern P. Control electronics 20 likewise can also be configured to control the position of mirror 70 and therefore, ultimately, the pattern P. In this way, pattern P, or any of its elements may be made to be perceived by the patient as blinking. Furthermore, the perception of both discrete spots and blinking may be accomplished by simply scanning quickly between elements of pattern P to limit the amount of light registered by the patient in those intermediate spaces.

The inherent flexibility of scanned light sources thus enables many desired clinical possibilities. A device such as this may be mounted directly onto, among other things, an ophthalmic visualization tool such as a slit lamp biomicroscope, indirect ophthalmoscope, fundus camera, scanning laser ophthalmoscope, or optical coherence tomography system.

There are other techniques for creating pattern P, such as by moving the light source(s) directly. Alternately, scanner 63 can comprise a two-dimensional acousto-optic deflector, or one or more optical elements with optical power that are translated. Mirror 70 may be tilted or translated (if there is surface curvature) to either act as the system scanner or augment beam movement already created by scanner 63. In the case where mirror 70 has optical power, compensating optical elements (not shown) may be required to produce an image, as opposed to a simple illumination. Similarly, the beam 30 could be divided using passive elements, such as diffractive optical elements (e.g. gratings or holograms), refractive elements (e.g. beam splitters, lenslet arrays, etc), or even active devices (e.g. adaptive optics) to create multiple beams simultaneously. These beams could then be deployed at once for an even more efficient treatment. They may also be used in conjunction with scanner 63 to provide a mixed approach.

The above described system 1 is configured to provide pulses of light or scanned light such that any targeted tissue receives treatment light only within a specific duration range in order to achieve the desired results of the present invention. Specifically, it has been discovered that treating any particular tissue location with pulsed or scanned light having a duration of $\tau_p$ within the range of $30\ \mu s \leq \tau_p < 10$ ms provides superior and unexpected results. 30 μs affects predominantly the 4 μm of pigmented tissue, and 10 ms nominally only a 75 μm thickness of tissue including the pigmented target, not the entire tissue thickness. This range of pulse durations confines the heat to the layers of tissue adjacent to the targeted pigmented layer without allowing for excessive thermal diffusion and high peak temperatures to be reached throughout the tissue volume. The average distance from the RPE to the outer nuclear layer of the sensory retina is approximately 80 μm. Unlike current approaches to selective treatments, the present invention causes confined photothermal damage. Thus, one may utilize the visible endpoint of a more traditional longer pulse duration burn (say, 20 or 50 ms) to extrapolate the heating effects for the shorter duration pulses of the present invention, allowing for spatially selective therapies without the need for complicated diagnostic devices. Specifically, this time duration of treatment provides spatially selective photothermal tissue damage while avoiding indiscriminant photomechanical tissue damage that results from the use of longer or shorter pulse durations, respectively. It has also been discovered that using a narrow bandwidth of light in the range between 400 and 700 nm provides superior results.

Unlike current approaches to ophthalmic photomedicine which uses pulse durations that are either exceedingly long and easily capable of causing photothermal damage to the entire tissue thickness (e.g. 100 ms pulses allowing heat to flow through the entire tissue during the pulse), or exceedingly short in an attempt to confine a photomechanical reaction to only the pigmented target (e.g. 1 μs pulses that confine the heat to melanosomes), the present invention provides for the use of pulse durations that allow for heat to flow into adjacent layers and structures without damaging the entire tissue, yielding unexpectedly superior clinical outcomes. The use of pulse durations, $\tau_p$, in the range of $30\ \mu s \leq \tau_p < 10$ ms provides for photothermal injury to specific tissue layers and structures not anticipated using currently available clinical laser systems and technologies. Specifically, the burns achieved using such pulse durations are not readily visible, but nonetheless create sufficient damage to produce defects under FA. This novel finding provides evidence of both the limited extent and clinical significance of the burns provided by the present invention.

Longer laser pulses (typically 100 ms, or greater) are routinely used simply because those were the pulse duration limits of the seminal clinical work accomplished in the 1970s showing the clinical benefit of using visible light lasers (argon ion and argon ion pumped dye lasers; operating at 514 nm and 577 nm, respectively) in lieu of the then standard arc lamp light sources used for retinal photocoagulation. The laser light sources used at that time were relatively low powered (~1 Watt) and limited in their ability to produce pulses shorter than 50 ms, let alone pulses capable of readily visible burns. The laser pulse durations used were arrived at as more or less a compromise between what was available and what was noticed to create a readily visible retinal burn. Even so, the use of lasers allowed for more precise burns to be created than was otherwise possible at the time.

The experimental use of microsecond pulses was an attempt to further distinguish selectivity over the existing standard of care (i.e. 100 ms pulses). However, the use of such microsecond pulses was an effort to confine a photomechanical reaction to a sub-cellular structure as a way to affect change in the tissue layer comprised of the host cells. Such extremely confined damage is impossible to discern using visual ophthalmoscopy. Like the present invention, it also leads to defects discernable under FA. However, predicting the results is complicated by the need to utilize an online monitoring scheme, such as the optoacoustic bubble cavitation detection approach described by Schuele, et al in *IOVS*, Vol. 46, No. 2 (2005). Cavitation is a photomechanical effect, and is created when a melanosome is heated to a point of boiling the surrounding intracellular water (estimated to occur at a temperature of 140° C.). Such severe localized heating is in contrast to the present invention, which provides, for the photothermal damage via relatively gently heating of a target and its adjacent tissue layers.

Thus, the above described system 1 is configured to either produce a pattern P of fixed spots where each spot lasts between 30 µs and 10 ms, or a moving beam that dwells on any given point on the target tissue a total of between 30 µs and 10 ms. Whatever the configuration, it is important that any treated portion of the target tissue "see" treatment light having a duration of between 30 µs and 10 ms. By adjusting the scan rate and spot size, one may tailor the dwell time (pulse duration) over any portion of this range. Thus, the term "pulse of light" is used herein to describe light that is directly pulsed with a particular time duration and delivered to the target tissue without intentional motion, as well as continuous light that is made to move over tissue within a particular time duration. There are practical concerns, however, such as hand and eye movement that must be overcome to provide precise treatment.

One may safely consider that the eye does not move appreciably over the course of 1 s when a patient contact lens 72 is used. The contact lens allows for visualization of the patient's eye, and dampens the movements of the patient's eye. Although, if the light is delivered to provide for the selective therapy described herein, one would likely need not be as concerned about inadvertently irradiating portions of the eye once thought taboo due to the collateral damage caused by known long pulse techniques. With the truly selective therapies described herein, one may very well be able to treat the entire retina without causing loss of vision.

Figure 6:
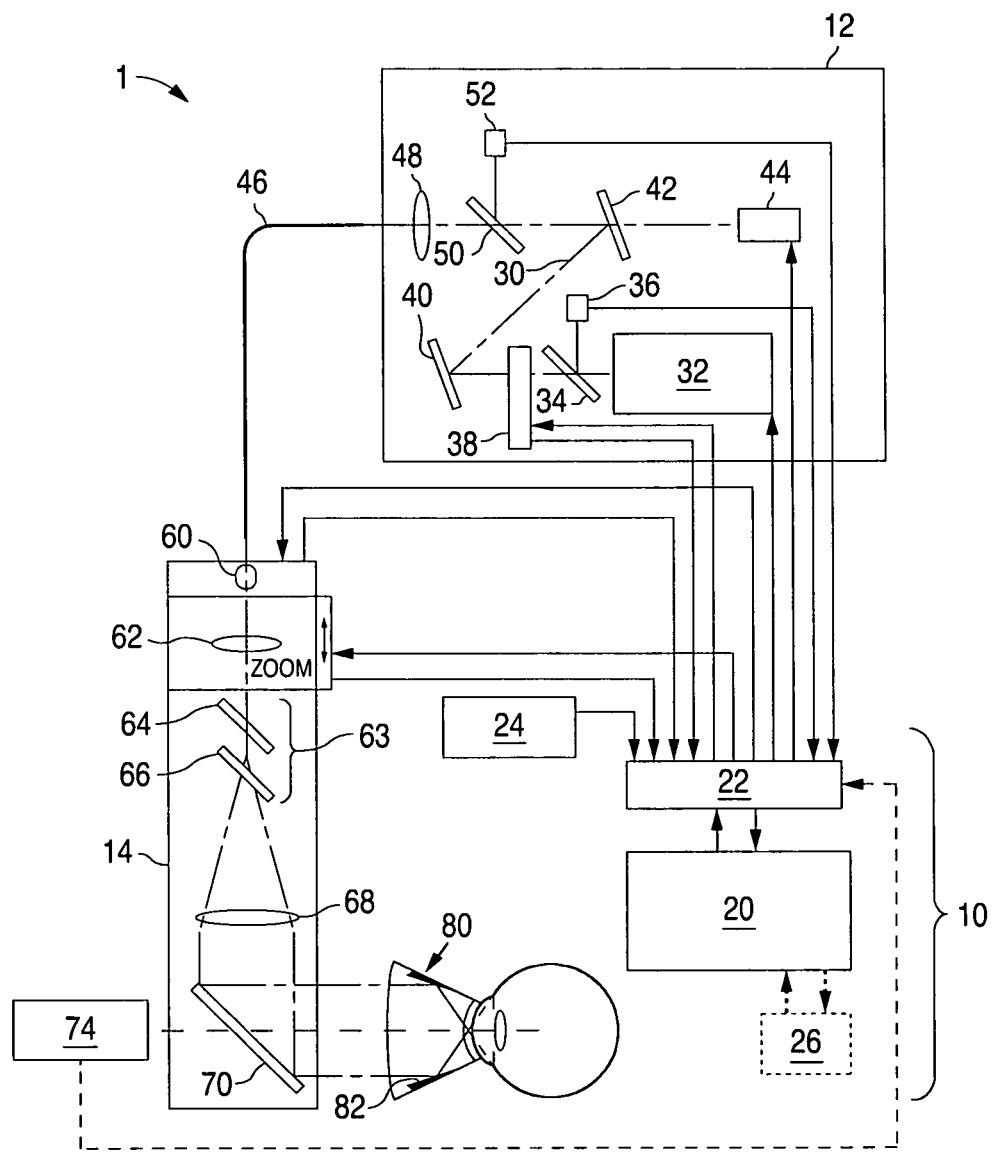
FIG. 6 is a diagram showing the elements of an alternate embodiment of the light generating and scanning system for implementing the present invention.

FIG. 6 shows an alternate embodiment of the system 1, which is particularly suited for the treatment of the trabecular meshwork (TM). Here the ophthalmic contact lens of FIG. 5 is replaced with a gonioscopic lens 80 with reflective side surfaces 82, which are optimized for directing the light at an acute angle towards the TM.

The above described treatment system has been reduced to practice, using a solid state laser light source 32 (e.g. a frequency-doubled Nd:YAG laser), producing a 2.5 W beam that is either scanned onto the target tissue in a continuous wave fashion, or is scanned to ultimately form a pattern of fixed spots on the target tissue. The system was used and tested in an animal model with long term follow up to confirm the effectiveness of eye treatment while keeping in mind the practical requirements of system robustness, cost-effectiveness, and efficiency. Pulses of the 532 nm light with durations of 500, 1000, and 5000 µs were scanned onto the retinas of Dutch-belted rabbits. Results were captured using both visible light photography and infrared fluorescein angiography (FA) from a Zeiss fundus camera at a constant magnification. For all three pulse durations, the damage was not visible without the aid of FA. This is evidence of the limited spatial extent of the approach, and its effect on the RPE. The sets of shorter duration pulses were each delivered inside a square region whose corners were defined by 100 ms burns. The 500 and 1000 µs pulses exhibited somewhat greater degrees of selectivity than the 5000 µs pulses. The short pulse (500, 1000, and 5000 µs) lesions showed much greater selectivity than the 100 ms marker burns. None of the short pulse lesions were ophthalmoscopically visible, unlike the 100 ms marker burns. Three such rabbits were treated in this study all with similar results.

Histological samples of the same tissue were also captured, which detail the effects at a microscopic level (~400×, original magnification). The spot diameter on the retina was ~130 µm. The pulse durations and powers used were as follows: 500 µs at 750 mW, 1000 µs at 500 mW, and 5000 µs at 150 mW. There was no apparent damage to either Bruch's membrane or the inner sensory retina in any of the images. Likewise, the images for the 500 and 1000 µs treatments show damage is confined to the vicinity of the RPE, while the image of the 5000 µs image shows a selective effect involving the inner sensory retina. In contrast, an image captured using a 50 ms, 90 mW, and 130 µm spot diameter long burn in a similar rabbit shows a full thickness retinal burn, as the long pulse allows for a significant amount of heat to dissipate to tissue surrounding the pigmented target.

Thus, it is clear that the use of visible light pulses between 30 µs and 10 ms to achieve heating predominantly in a pigmented layer of biological tissue produces results superior and unexpected relative to the shorter or longer pulses currently used. The use of optical pulses of visible light to achieve heating predominantly only in nearby a pigmented layer of biological tissue avoids significant photothermal damage to adjacent tissue layers. This translates into power densities I in the range of $1 \text{ W cm}^{-2} \leq I \leq 100 \text{ kWcm}^{-2}$. These light pulses can be achieved using a stationary beam of pulsed therapeutic light, pulsed light scanned to create patterns on the target tissue sequentially, a pulsed beam divided to create patterns on the target tissue simultaneously, a pulsed beam that is both divided and scanned, pulses of light achieved by moving the therapeutic beam over the target tissue at a particular rate to ensure the length of exposure is limited to between 30 µs and 10 ms, and where the beam is both gated and moved over tissue to allow some of the target tissue to be untreated.

It is to be understood that the present invention is not limited to the embodiment(s) described above and illustrated herein, but encompasses any and all variations falling within the scope of the appended claims.

What is claimed is:

1. A method of treating ophthalmic tissue adjacent to a retinal pigmented epithelium or ophthalmic tissue adjacent to a pigmented portion of a trabecular meshwork of an eye, comprising:
   generating a beam of light;
   deflecting the beam of light into a pattern;
      wherein at least one of the generating and the deflecting causes the beam of light to comprise a plurality of light pulses; and
   delivering the pattern of light pulses through a cornea to the retinal pigmented epithelium or the pigmented portion of the trabecular meshwork of the eye, wherein:

each light pulse of the pattern of light pulses is delivered for a duration of between 30 μs and 10 ms, each light pulse of the pattern of light pulses has a wavelength of between 400 and 700 nm, and each light pulse of the pattern of light pulses has a power intensity of less than or equal to 100 kW/cm².

2. The method of claim 1, wherein the generating is performed using a pulsed light source.

3. The method of claim 1, wherein the generating of the light beam includes periodically shuttering the light beam to create the plurality of light pulses.

4. The method of claim 1, wherein the deflecting is performed using one or more moving optical elements.

5. The method of claim 4, wherein the pattern comprises a plurality of discrete and stationary spots.

6. A method of treating ophthalmic tissue adjacent to a retinal pigmented epithelium or ophthalmic tissue adjacent to a pigmented portion of a trabecular meshwork of an eye, comprising:

generating a beam of light;

deflecting the beam of light into a pattern;

delivering the pattern through a cornea to the retinal pigmented epithelium or the pigmented portion of the trabecular meshwork of the eye, wherein:

the pattern comprises a moving beam of light that dwells on a given point for a duration of between 30 μs and 10 ms, the moving beam of light has a wavelength of between 400 and 700 nm, and each given point receives light having a power intensity of less than or equal to 100 kW/cm².

7. The method of claim 6, wherein the deflecting is performed using one or more moving optical elements.

8. The method of claim 6, wherein the pattern comprises at least a straight or a curved line.

9. The method of claim 1, further comprising:
causing photocoagulation of the ophthalmic tissue adjacent to the retinal pigmented epithelium of the eye.

10. The method of claim 1, further comprising:
causing photocoagulation of the ophthalmic tissue adjacent to the pigmented portion of the trabecular meshwork of the eye.

11. The method of claim 6, further comprising:
causing photocoagulation of the ophthalmic tissue adjacent to the retinal pigmented epithelium of the eye.

12. The method of claim 6, further comprising:
causing photocoagulation of the ophthalmic tissue adjacent to the pigmented portion of the trabecular meshwork of the eye.

* * * * *